United States Patent [19]

Sekiya

[11] Patent Number: 5,776,906
[45] Date of Patent: Jul. 7, 1998

[54] METHOD FOR PROMOTING FAT-DEGRADATION IN FAT CELLS

[75] Inventor: Keizo Sekiya, Zentsuji, Japan

[73] Assignee: Director General of Shikoku National Agricultural Experiment Station, Ministry of Agriculture, Forestry and Fisheries, Zentsuji, Japan

[21] Appl. No.: 755,257

[22] Filed: Nov. 22, 1996

[30] Foreign Application Priority Data

Sep. 13, 1996 [JP] Japan .................... 8-263773

[51] Int. Cl.⁶ .................... A61K 31/70; A61K 31/35
[52] U.S. Cl. .................... 514/27; 514/456; 514/909
[58] Field of Search .................... 514/27, 456, 909

[56] References Cited

U.S. PATENT DOCUMENTS 5,506,211  4/1996  Barnes et al. .................... 514/27

*Primary Examiner*—Kimberly Jordan
*Attorney, Agent, or Firm*—Oblon, Spivak, McClelland, Maier & Neustadt, P.C.

[57] ABSTRACT

For the purpose of providing a composition having an ability of promoting degradation of accumulated cellular fats, a substance having such ability was developed from naturally-occurring safe materials. Thus, according to the present invention, a composition for promoting fat-degradation in a fat cell comprising containing an isoflavone in an amount effective to promote the fat-degradation in said fat cell.

6 Claims, 4 Drawing Sheets

METHOD FOR PROMOTING FAT-DEGRADATION IN FAT CELLS

FIELD OF THE INVENTION

The present invention relates to a composition for promoting fat-degradation (lipolysis) in fat cells, more specifically to a composition having an ability of promoting degradation of accumulated fat in fat cells.

BACKGROUND INFORMATION

Vital hormones such as noradrenaline, adrenaline and glucagon are known to have promoting fat-degradation effect. Caffeine and theophylline were also reported to have promoting fat-degradation effects.

In addition, so-called weight-reducing composition which serves to degrade a somatic fat to make a fat cell smaller, whereby providing a slim body have been studied, and that containing kola seed extract (Japanese Patent Application Kokai Hyo 3-504241) and that containing a fat-degrading substance (lipolytic substance) such as caffeine in combination with a growth factor (Japanese Patent Application Kokai Hyo 6-506668) were reported to be effective.

However, hormones and caffeine involves problems when used for a prolonged period for the purpose of weight-reducing since they may cause adverse effects.

SUMMARY OF THE INVENTION

As a result of conducting the studies in order to develop a substance having an ability of promoting degradation of fat from a naturally-occurring material which has no problems with regard to safety, we finally found that a soybean extract has such activity and that the active ingredient is an isoflavone. Based on such findings, this invention is established.

Accordingly, the present invention provides a composition for promoting fat-degradation in a fat cell which comprises containing an isoflavone and/or its derivative in an amount effective to promote the degradation of fat in the fat cell.

DETAILED DESCRIPTION OF THE PREFERRED EMBODIMENTS

Figure 1:
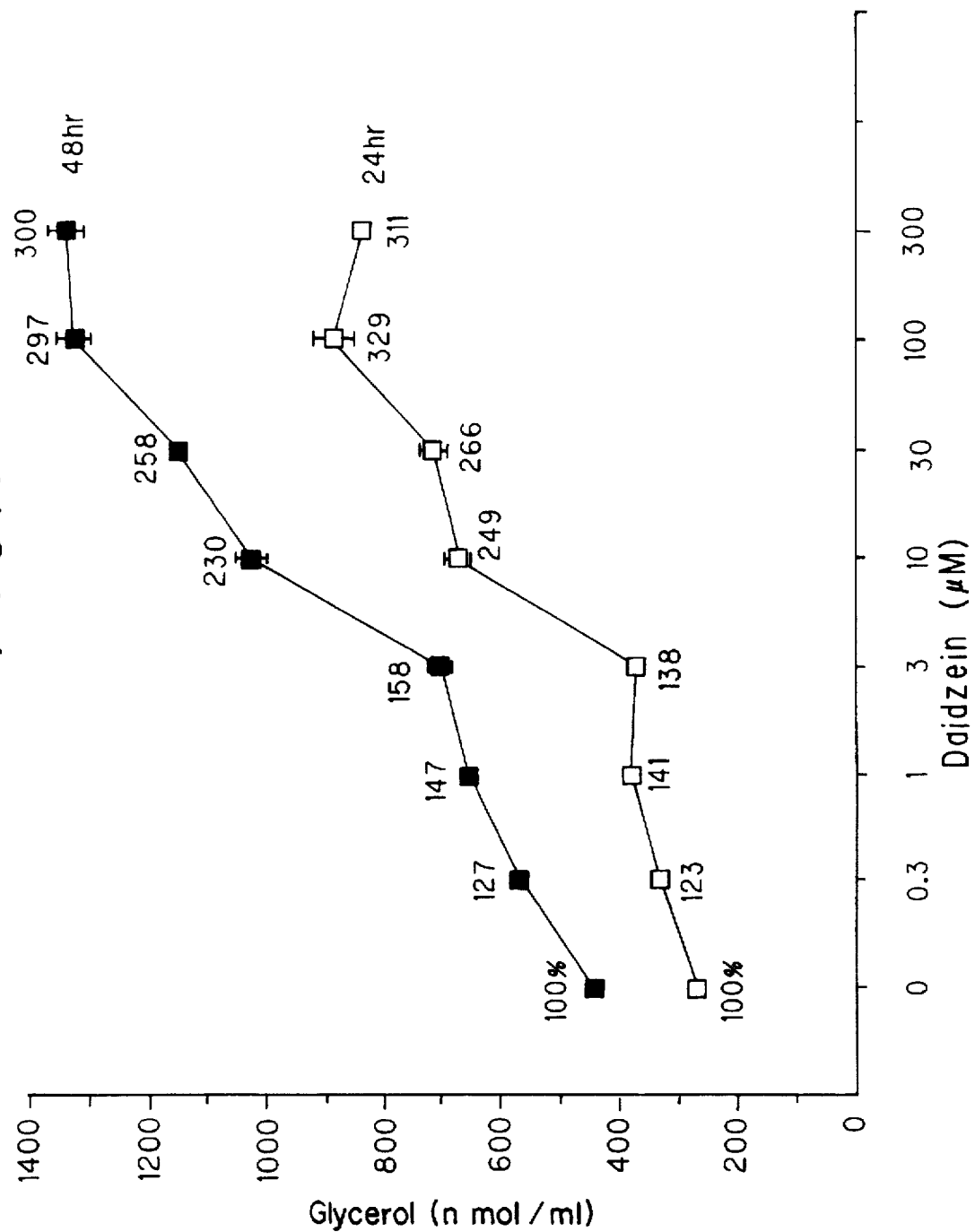
FIG. 1 is a graph indicating the promoting fat-degradation effect of daidzein.

An isoflavone employed in the present invention is a component contained in bean plants such as soybean, and daidzein, daidzin, genistein, genistin and derivatives thereof are included in the isoflavone. These compounds may be employed independently or in combination. The content of an isoflavone in a composition according to the present invention is an amount effective to promote degradation of fat in a fat cell, and may be determined in view of the intended use of the composition. For example, an isoflavone is contained in an amount of 0.05 to 1,000,000 µg/ml (g) when the composition is intended to be used as a pharmaceutical for injection or infusion, while it is contained in an amount of 5 to 1,000 mg/ml (g) when the composition is intended to be used as a food or pharmaceutical in forms of solid, liquid, powder, granule, paste and the like for oral or percutaneous administration. An isoflavone is contained in an amount of 5 to 1,000 mg/ml (g) when the composition is intended to be used as a feed for domestic animals in forms of solid, liquid, powder, granule, paste and the like.

In any intended use described above, a content of an isoflavone in a composition less than a lowest effective amount results in no satisfactory fat-degradation effect in a fat cell.

Although any commercially available isoflavones may be used, those obtained from a soybean by extraction may also be employed. The extraction may be conducted by an ordinary method using an organic solvent such as methanol, ethanol, butanol and diethylether, for example, as described below.

To 1 kg of soybean flake, 1 to 3 liters of an organic solvent such as methanol is added and the mixture is extracted while heating under reflux to obtain an extract. The extract is concentrated to dryness and the residue is admixed with each 100 to 1,000 ml of water and an organic solvent such as n-butanol, and stirred. Subsequently, the mixture is allowed to stand to separate into a water layer and a butanol layer.

Then the butanol layer is concentrated to dryness, and the residue is taken into an organic solvent such as diethylether and stirred. Subsequently, the mixture is centrifuged to obtain a sediment which is then admixed with ether to remove soluble substances. The ether-insoluble substance thus obtained (sediment) is recovered as an isoflavone-containing fraction. Then, using an ordinary procedure such as chromatography if necessary, each component is fractionated. The isoflavones can be identified by any methods such as thin layer chromatography.

As described above, a commercial pure product of an isoflavone may be employed as it is in a composition according to the invention, while a crude product extracted from a bean plant or a preparation purified therefrom may also be employed. If necessary, customary additives such as a bulking agent, stabilizer, excipient etc., may be incorporated to prepare a composition. The composition may be in forms of solid, liquid, powder, granule, paste etc., depending on intended uses.

Since a composition promoting fat-degradation according to the present invention has an ability of degrading a fat to exhibit a weight-reducing effect, it may be useful in the fields of pharmaceuticals, cosmetics, functional foods and the like, and may be utilized as various formulations for percutaneous administration (application onto skins), oral administration and intravenous injection, or may be added to a food. In addition, the composition may be added to a feed for domestic animals since it degrades fats whereby contributing to the production of a low fat meat.

A composition promoting fat-degradation according to the present invention exhibits an excellent fat-degradation effect at a relatively low concentration. Using this effect, the composition can be utilized as a cosmetic, pharmaceutical or functional food product having a weight-reducing effect.

In addition, the active ingredient in the composition is highly safe since it is an edible naturally-occurring component contained in a soybean and other plants, and has been ingested for a long period.

EXAMPLES

The present invention is further illustrated in the following examples, which are not intended to restrict the scope of the invention.

Production Example 1

To 1 kg of soybean flake, 3 liters of methanol were added and the mixture was extracted while heating under reflux to obtain an extract which was then concentrated to dryness in a rotary evaporator. The residue thus obtained was admixed with each 500 ml of water and n-butanol and shaked and stirred, and then allowed to stand to separate into water layer and butanol layer. The butanol layer was dried under reduced pressure and then admixed with diethylether and shaked and stirred. Subsequently, centrifugation was conducted (3,000 rpm, 10 minutes) and supernatant ether-soluble substances were removed to obtain a sediment, which the procedure of adding ether and removing the soluble substances was coducted repeatedly for several times. The ether-insoluble substances thus obtained were recovered as an isoflavone-containing fraction.

Production Example 2

From the fraction obtained in Production example 1, daidzein, daidzin, genistein and genistin were isolated by reverse HPLC (using an ODS column, eluted with a gradient from 0 to 50% acetonitrile in 0.1% aqueous solution of trifluoroacetic acid, absorbance detection at 262 nm).

Example 1

A fat cell precursor (preadipocyte) 3T3-L1 derived from a mouse was incubated in DME medium (Dulbecco's modified Eagle medium) supplemented with 10% fetal bovine serum in 6-well multiplate at 37° C. The culture medium was replaced every 2 or 3 days. After the cell growth was confluenced, dexamethasone, methylisobutylxanthine and insulin were added to the culture medium to induce differentiation into a fat cell. Differentiation induction treatment was performed for 2 days, and thereafter the incubation was continued in the initial medium.

After about 1 week, to 3T3-L1 cell which had been differentiated into a fat cell, a certain amount of daidzein obtained in Production Example 2 was added,followed by incubation. Then, after 1 day (24 hours) and 2 days (48 hours), the amount of glycerol in the culture medium was determined as an index of the fat-degradation. Glycerol was released by the fat-degradation, and determined by colorimetry using glycerol oxidase and the like.

The results are shown in FIG. 1. As evident from the figure, daidzein induced the fat-degradation dose-dependently. Since daidzein was effective at the concentration relatively as low as 0.3 µM, i.e., 0.0763 µg/ml (or g), it is expected to exhibit similar in vivo effectiveness. In the figure, the abscissa represents daidzein concentration (µM), while the ordinate represents the amount of glycerol released as a result of the fat-degradation. □ and ■ indicate fat-degradation effect of 24 and 48 hours after addition of daidzein, respectively, and the values in the figure are the amount of glycerol derived from various concentrations of daidzein which were calculated based on the amount of glycerol derived from 0 µM of daidzein (100%).

Example 2

Figure 2:
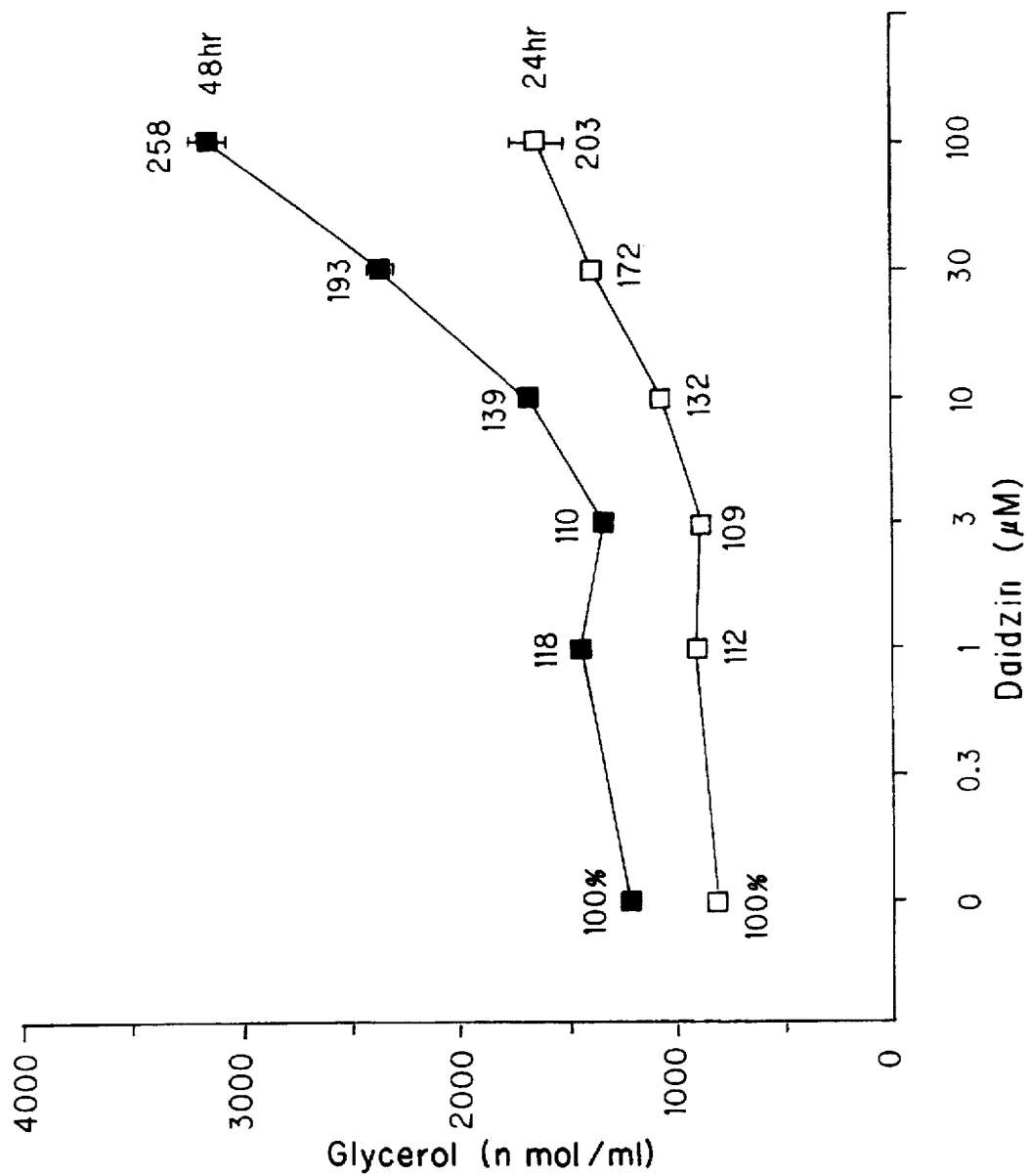
FIG. 2 is a graph indicating the promoting fat-degradation effect of daidzin.

This Example was conducted similarly to Example 1 except for using daidzin instead of daidzein. The results are shown in FIG. 2. Legends are similar as in Example 1. As evident from the figure, daidzin caused the fat-degradation dose-dependently. Since daidzin showed such results at a relatively low concentration, it is expected to exhibit similar in vivo effectiveness.

Example 3

Figure 3:
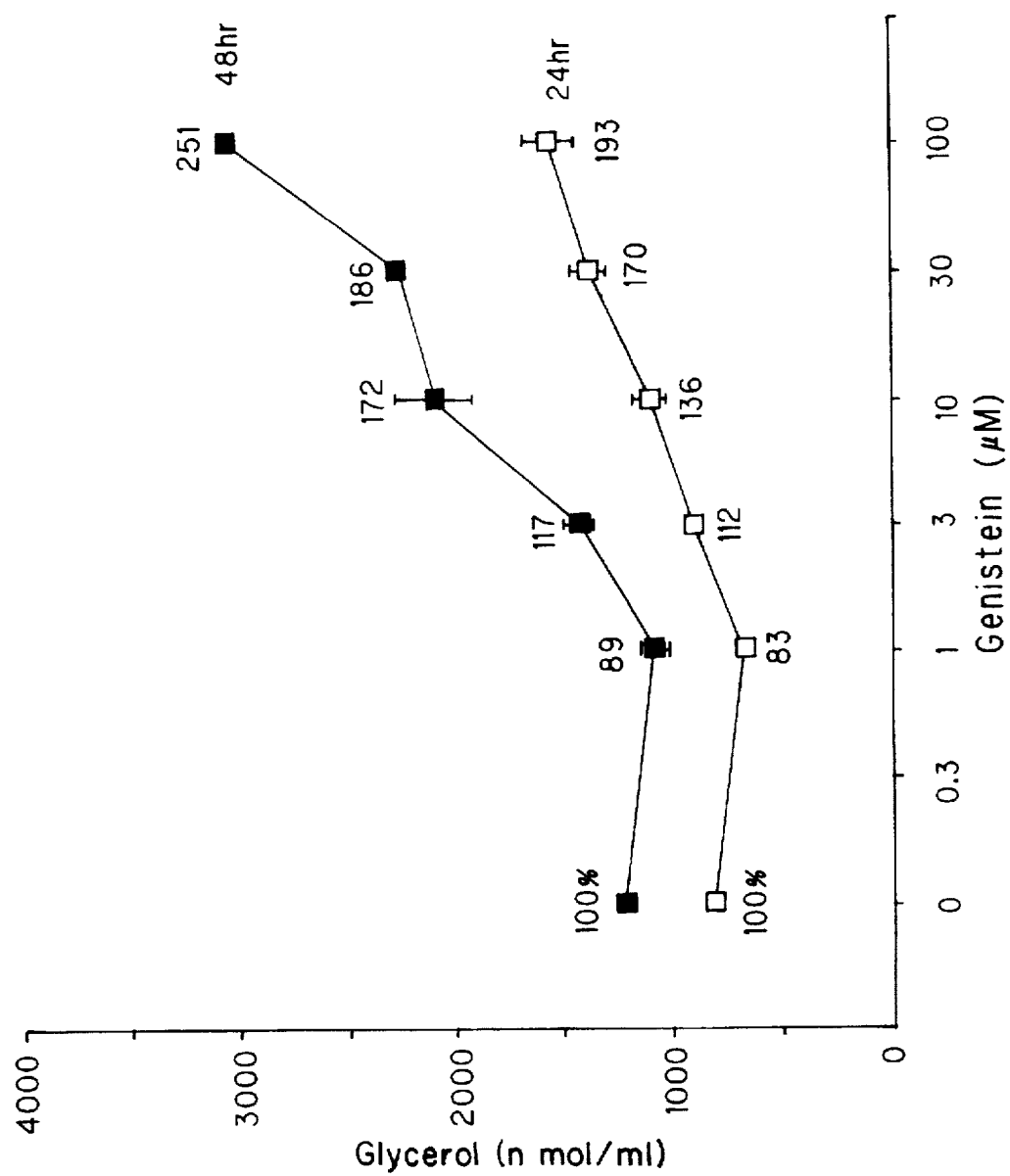
FIG. 3 is a graph indicating the promoting fat-degradation effect of genistein.

This Example was conducted similarly to Example 1 except for using genistein instead of daidzein. The results are shown in FIG. 3. Legends are similar as in Example 1. As evident from the figure, genistein caused the fat-degaration dose-dependently. Since genistein showed such results at a relatively low concentration, it is expected to exhibit similar in vivo effectiveness.

Example 4

Figure 4:
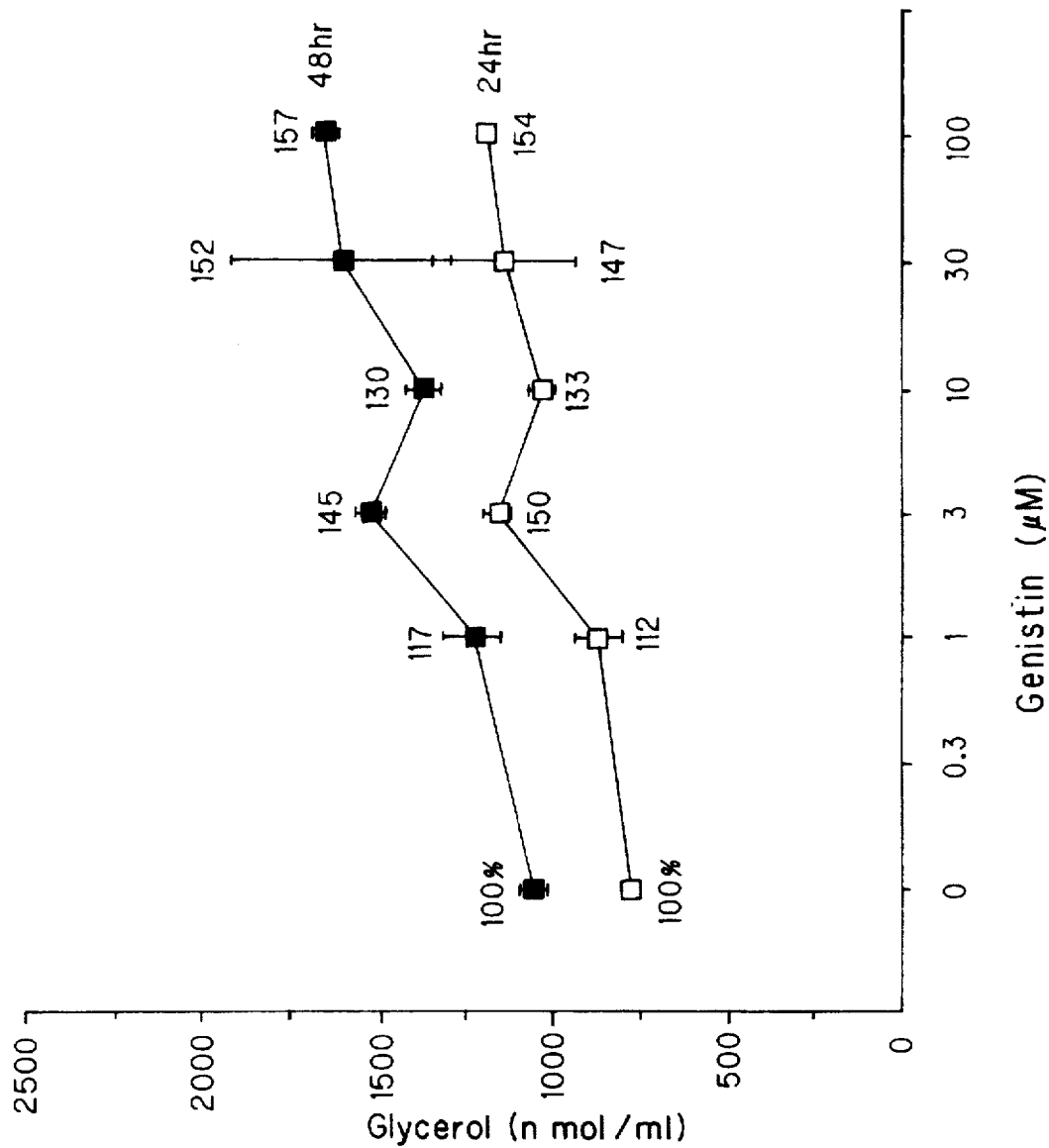
FIG. 4 is a graph indicating the promoting fat-degradation effect of genistin.

Example 4 was conducted similarly to Example 1 except for using genistin instead of daidzein. The results are shown in FIG. 4. Legends are similar as in Example 1. As evident from the figure, genistin caused the fat-degradation dose-dependently. Since genistin showed such results at a relatively low concentration, it is expected to exhibit similar in vivo effectiveness.

Example 5

Daidzein (67 mg/kg body weight) was administered intraperitoneally to a mouse, and serum glycerol was measured after 24 hours, during which the animal was allowed to take water freely, but was fasted. Daidzein was administered as a suspension in lecithin solution (5 mg/ml).

The results are shown in Table 1. As evident from the table, the glycerol level was increased significantly in the daidzein treatment group when compared with the control group. Based on such findings, daidzein was demonstrated to promote the degradation of fat in vivo similarly as in the cell culture.

TABLE 1

Fat-degradation promoting effect of daidzein in mice

| Treatment group | Serum glycerol after 24 hours (n mol/ml) |
|---|---|
| Control group (vehicle i. p.) | 12.9 ± 1.1 |
| Daidzein group (i.p., 67 mg/kg) | 20.4 ± 4.3* |

*: Significant difference, $p < 1\%$

What is claimed is:

1. A method for promoting fat degradation in a fat cell comprising the step of administering to a human a composition containing an effective amount of an isoflavone, thereby promoting fat degradation in the fat cell.
2. The method of claim 1, wherein the composition is in the form of a solid, a liquid, a powder, or a paste.
3. The method of claim 1, wherein the composition further contains a bulking agent, a stabilizer, or an excipient.
4. The method of claim 1, wherein the isoflavone is daidzein, daidzin, genistein, or genistin.
5. The method of claim 1, wherein the composition is administered orally or percutaneously.
6. The method of claim 1, wherein the composition is administered by injection or infusion.

* * * * *